United States Patent
Saelinger et al.

(10) Patent No.: US 11,358,922 B2
(45) Date of Patent: Jun. 14, 2022

(54) PROCESS FOR PREPARING 4-CHLOROBENZYL PROPARGYL ETHER

(71) Applicant: BASF SE, Ludwigshafen (DE)

(72) Inventors: Daniel Saelinger, Ludwigshafen (DE); Philip Muelheims, Ludwigshafen (DE); Helmut Zech, Ludwigshafen (DE); Roland Goetz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/756,961

(22) PCT Filed: Oct. 31, 2018

(86) PCT No.: PCT/EP2018/079887
§ 371 (c)(1),
(2) Date: Apr. 17, 2020

(87) PCT Pub. No.: WO2019/086545
PCT Pub. Date: May 9, 2019

(65) Prior Publication Data
US 2020/0331829 A1  Oct. 22, 2020

(30) Foreign Application Priority Data
Nov. 2, 2017 (EP) .................................. 17199691.1

(51) Int. Cl.
*C07C 41/16* (2006.01)
*C07C 43/176* (2006.01)
*C07C 41/01* (2006.01)
*C07C 43/166* (2006.01)

(52) U.S. Cl.
CPC .............. *C07C 41/16* (2013.01); *C07C 41/01* (2013.01); *C07C 43/166* (2013.01); *C07C 43/176* (2013.01)

(58) Field of Classification Search
CPC .................................................. C07C 43/176
See application file for complete search history.

(56) References Cited

FOREIGN PATENT DOCUMENTS

| CN | 104945457 A | * | 9/2015 |
|---|---|---|---|
| WO | WO-2016/075289 A1 | | 5/2016 |
| WO | WO-2017/093925 A1 | | 6/2017 |
| WO | WO-2017/102905 A1 | | 6/2017 |
| WO | WO-2017/133942 A1 | | 8/2017 |
| WO | WO-2017/144336 A1 | | 8/2017 |
| WO | WO-2017/144337 A1 | | 8/2017 |
| WO | WO-2017/215928 A1 | | 12/2017 |
| WO | WO-2017/215929 A1 | | 12/2017 |
| WO | WO-2018/050518 A1 | | 3/2018 |
| WO | WO-2018/082964 A1 | | 5/2018 |
| WO | WO-2018/083040 A1 | | 5/2018 |
| WO | WO-2018/091338 A1 | | 5/2018 |
| WO | WO-2018/141642 A1 | | 8/2018 |
| WO | WO-2018/149676 A1 | | 8/2018 |
| WO | WO-2018/172109 A1 | | 9/2018 |
| WO | WO-2018/177907 A1 | | 10/2018 |
| WO | WO-2018/197541 A1 | | 11/2018 |
| WO | WO-2018/202654 A1 | | 11/2018 |
| WO | WO-2018/210662 A1 | | 11/2018 |
| WO | WO-2018/210663 A1 | | 11/2018 |
| WO | WO-2018/229027 A1 | | 12/2018 |
| WO | WO-2019/016115 A1 | | 1/2019 |
| WO | WO-2019/086545 A1 | | 5/2019 |

OTHER PUBLICATIONS

Xiao et al. "Zinc Iodide-Mediated Direct Synthesis of 2,3-Dihydroisoxazoles from Alkynes and Nitrones"Adv. Synth. Catal. 2016, 358, 1859- 1863 and supporting information pp. S1-S100) (Year: 2016).*
Louvel et al. "Removal of Human Ether-à-go-go Related Gene (hERG) K+ Channel Affinity through Rigidity: A Case of Clofilium Analogues" J. Med. Chem. 2013, 56, 9427-9440 and supporting information pages S1-S13 (Year: 2013).*
Patent No. CN104945457B, English translation, Sep. 2015, pp. 1-13 (Year: 2015).*
Desikan, S. "Studies in immobilized phase transfer catalysis" Published 1997, pp. 1-163 (Year: 1997).*
European Patent Application No. 17199691.1, Extended European Search Report, dated Apr. 10, 2018.
International Application No. PCT/EP2018/079887, International Search Report and Written Opinion, dated Apr. 2, 2019.
Koch et al., Process development of a dual MMP/TNF inhibitor (SDZ 242-284), Org. Process Res. Dev., 6(5):652-659 (2002).
Montevecchi et al., Substituent Effects on Vinyl Radical Cyclizations Onto Aryl Rings, J. Org. Chem., 63(3):537-42 (1998).
Teoh et al., Sustainability Improvements through Catalyst Recycling in a Liquid-Liquid Batch and Continuous Phase Transfer Catalyzed Process, Org. Process Res. Dev., 21(4):520-530 (2017).

* cited by examiner

*Primary Examiner* — Medhanit W Bahta
(74) *Attorney, Agent, or Firm* — Marshall, Gerstein & Borun LLP

(57) ABSTRACT

The present invention relates to a process for preparing 4-chlorobenzyl propargylether comprising a step (a) of reacting 4-chlorobenzyl chloride with propargyl alcohol in the presence of a base and a phase transfer catalyst, wherein the reaction mixture comprises at least two phases, wherein one phase is an organic phase and one phase is an aqueous phase.

16 Claims, No Drawings

PROCESS FOR PREPARING 4-CHLOROBENZYL PROPARGYL ETHER

This is the U.S. national phase of International Patent Application No. PCT/EP2018/079887, filed Oct. 31, 2018, which claims the benefit of European Patent Application No. 17199691.1, filed Nov. 2, 2017.

The present invention relates to a process for preparing 4-chlorobenzyl propargyl ether comprising a step (a) of reacting 4-chlorobenzyl chloride with propargyl alcohol in the presence of a base and a phase transfer catalyst, wherein the reaction mixture comprises at least two phases, wherein one phase is an organic phase and one phase is an aqueous phase.

Nitrogen is an essential element for plant growth and reproduction. About 25% of the plant-available nitrogen in soils (ammonium and nitrate) originates from decomposition processes (mineralization) of organic nitrogen compounds such as humus, plant and animal residues and organic fertilizers. Approximately 5% derive from rainfall. On a global basis, the biggest part (70%), however, are supplied to the plants by inorganic nitrogen fertilizers. Without the use of nitrogen fertilizers, the earth would not be able to support its current population.

Soil microorganisms convert organic nitrogen to ammonium ($NH_4^+$) which is subsequently oxidized to nitrate ($NO_3^-$) in a process known as nitrification. Albeit very important for agriculture, nitrate is highly mobile in the soil and may be readily lost from soils by leaching to ground water. Nitrogen is further lost by microbiological denitrification to gaseous forms of nitrogen. As a result of the various losses, approximately 50% of the applied nitrogen is lost during the year following fertilizer addition (cf. Nelson and Huber; Nitrification inhibitors for corn production (2001), National Corn Handbook, Iowa State University).

As countermeasures the use of nitrification inhibitors, mostly together with fertilizers, was suggested. According to WO/2016/075289 benzyl propargyl ethers are suitable for use as nitrification inhibitors. One particularly advantageous benzyl propargyl ether is 4-chlorobenzyl propargyl ether.

Therefore, a need exists for an advantageous process for preparing 4-chlorobenzyl propargyl ether.

SU(11)1773901 A1 discloses a process for preparing benzyl propargyl ethers comprising the step of reacting benzyl chloride with cis-3-chloropropen-1-ol in the presence of a phase transfer catalyst.

Montevecchi et al. (Journal of Organic Chemistry, 1998, 63, 537-542) disclose a process for preparing benzyl propargyl ethers comprising reacting a benzyl chloride with propargyl alcohol in an organic solvent in the presence of sodium hydride.

CH568707 discloses insecticidal compounds and their preparation by reacting either propargyl alcohols with benzyl halogenides or propargyl halogenides with benzyl alcohols in the presence of different bases.

U.S. Pat. No. 3,946,040 discloses a process for preparing benzyl propargyl ethers by reacting benzyl alcohols with propargyl bromide in the presence of sodium hydride.

Teoh et al. (Organic Process Research and Development, 2017, DOI: 10.1021/acs.oprd.6b00337) disclose the O-alkylation of 3-phenyl-1-propanol in a three phase system in the presence of tetrabutylammonium bromide as phase transfer catalyst.

However, the processes for preparing benzyl propargyl ethers described in the prior art have disadvantages, e.g., in that they are not suitable for large-scale application because expensive starting materials, catalysts or bases are used. Moreover, the long reaction times are disadvantageous for large-scale application.

Furthermore, in cases were multiphase systems are present in the reaction mixture, the reduction of organic compounds in the wastewater has not been addressed. Moreover, the use of phase transfer catalysts is expensive and therefore economically disadvantageous, if the phase transfer catalyst is not recycled. On the other hand, the use of water as a reaction solvent is desirable in order to reduce the use of organic solvents.

It was therefore an object of the present invention to provide an improved process for preparing 4-chlorobenzyl propargyl ether, which is suitable for large-scale application. In this regard, it is a further object to reduce the reaction time of the process and reduce the formation of byproducts.

It is a further object of the present invention to provide a process, which is economically advantageous in terms of the used starting materials, catalysts and bases. It is a further object to provide an environmentally improved process with a view to the wastewater.

It has surprisingly been found that at least some of the above objectives can be achieved by the subject matter of the present invention as described hereinafter and in independent claim 1 and the claims depending thereon.

In one embodiment, the present invention relates to a process for preparing a compound of formula I

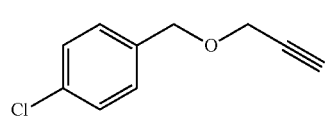

comprising a step (a) of reacting a compound of formula II

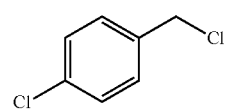

with a compound of formula III

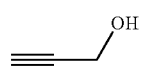

in the presence of a base and a phase transfer catalyst, wherein the reaction mixture comprises at least two phases, wherein one phase is an organic phase and one phase is an aqueous phase.

It has been surprisingly found by the inventors, that the process of the invention is suitable for large-scale application and provides the desired product in a short reaction time in a high purity. Furthermore, it is possible to recycle the phase transfer catalyst in order to reduce the TOC (total organic carbon) content of the wastewater. Moreover the TOC (total organic carbon) and/or AOX (adsorbable organic halides) content of the wastewater can be further reduced by extracting the aqueous phase after phase separation.

Further embodiments of the present invention can be found in the claims and the description. It is to be understood that the features mentioned above and those still to be illustrated below of the subject matter of the invention are preferred not only in the respective given combination, but also in other combinations without leaving the scope of the invention.

In connection with the above aspects of the present invention, the following definitions are provided.

As used herein, the compound of formula I represents 4-chlorobenzyl propargyl ether (CAS number: 4039-86-5), which is suitable for use as a nitrification inhibitor. In the context of the present invention the compound of formula I is obtained by reacting 4-chlorobenzyl chloride, i.e. the compound of formula II, with propargyl alcohol, i.e. the compound of formula III, in the presence of a base and a phase transfer catalyst.

The compound of formula II represents 4-chlorobenzyl chloride (CAS number: 100-44-7). 4-Chlorobenzyl chloride is a commercially available, inexpensive compound and therefore especially suitable as a starting material in a large-scale process.

The compound of formula III represents propargyl alcohol (CAS number: 107-19-7). Propargyl alcohol is a commercially available, inexpensive compound and therefore also suitable as a starting material in a large-scale process.

As used herein, the compound of formula I is provided by reacting the compound of formula II and the compound of formula III in the presence of a base. Suitable bases generally include alkali metal and alkaline earth metal hydroxides, alkali metal and alkaline earth metal oxides, alkali metal and alkaline earth metal carbonates, alkali metal and alkaline earth metal hydrogen carbonates, alkali metal and alkaline earth metal alcoholates, and nitrogen containing bases including tertiary amines, pyridines, and bicyclic amines. Preferred bases according to the invention include alkali and alkaline earth metal carbonates and hydrogen carbonates, alkali and alkaline earth metal hydroxides, and mixtures thereof. Particularly preferred bases are alkali hydroxides, especially sodium hydroxide.

As used herein, the process for preparing 4-chlorobenzyl propargylethers further involves the application of a phase transfer catalyst. A phase transfer catalyst is a catalyst that facilitates the migration of a reactant from one phase into another phase where the reaction occurs. This is typically relevant, when the reaction mixture comprises an organic phase and an aqueous phase, and one reactant is more soluble in the aqueous phase and the other reactant is more soluble in the organic phase. The phase transfer catalyst then facilitates a reaction of these two reactants with each other. Typical examples for phase transfer catalysts, especially in connection with anionic reactants, are quaternary ammonium salts. Commercially important catalysts include benzyltrimethylammonium chloride, benzyltriethylammonium chloride, tetraethylammonium chloride, tetrapropylammonium bromide, tetrabutylammonium bromide and tributylmethylammonium chloride. According to the present invention, a particularly preferred phase transfer catalyst in terms of the reduction of the reaction time is tributylmethylammonium chloride.

As used herein, the expression "the reaction mixture comprises at least two phases" describes a heterogeneous reaction mixture comprising at least two immiscible phases. According to the present invention, one phase is an organic phase and one phase is an aqueous phase. Typically, the two different phases are formed by using two immiscible solvents, e.g., water and an organic solvent, which is immiscible with water. The solvent with the lower density will form the upper layer of the two-phase system, and the solvent with the higher density will form the lower layer of the two-phase system. It is to be understood that stirring is preferably used in order to increase the interfacial area of the two phases and thus optimize the reaction. Various emulsification techniques have been developed to produce droplets from micrometer to nanometer scale. For details in this regard, reference is made to Keti Piradashvili et al., Chem. Rev. 2016, 116, 2141-2169. In the context of the present invention, 4-chlorobenzyl chloride is predominantly present in the organic phase and propargyl alcohol is typically predominantly present in the aqueous phase. The addition of a phase transfer catalyst, which is soluble in both phases, may facilitate the transfer of, e.g., the propargyl alcohol or propargyl alcoholate, which is formed after deprotonation with a base, from the aqueous phase to the organic phase.

It is also possible according to the present invention, that the reaction mixture comprises at least one additional phase. Preferably, a solid phase comprising a salt is formed during the reaction. In particular, a solid phase comprising sodium chloride may be formed during the reaction, if, e.g., sodium hydroxide is used as a base.

As indicated above, the term "organic phase" preferably refers to a phase comprising an organic solvent, wherein preferably the benzyl chloride is dissolved at the beginning of the reaction. Furthermore, the propargyl alcohol may at least partly be present in the organic phase. However, it is to be understood that the organic phase does not necessarily have to comprise an organic solvent. Instead, the organic phase may also be formed by the reactant 4-chlorobenzyl chloride, or later on by the product 4-chlorobenzyl propargyl ether. However, it is preferred according to the invention that the organic solvent comprises an organic solvent.

As used herein, the term "organic solvent" preferably refers to an organic solvent that, when mixed with water, is capable of forming a separate phase, i.e. is immiscible with water. Preferred organic solvents include alkanes, aromatic solvents and ethers, or mixtures thereof. Preferred alkane solvents include aliphatic hydrocarbons such as pentane, hexane, heptane, cyclohexane, petroleum ether, or mixtures thereof. Preferred aromatic solvents are e.g. benzene, toluene, xylene (ortho-xylene, meta-xylene or para-xylene), mesitylene, or mixtures thereof. A particularly preferred aromatic solvent is toluene. Preferred ethers are open-chained and cyclic ethers, in particular diethyl ether, methyl-tert-butyl-ether (MTBE), 2-methoxy-2-methyl-butane, cyclopentylmethylether, 2-methyltetrahydrofuran, or mixtures thereof.

As used herein, the term "aqueous phase" refers to a phase comprising water. Preferably the aqueous phase further comprises the base as used in the process of the invention. Furthermore, the propargyl alcohol will at least partly be present in the aqueous phase and will preferably react with the base, so that it will at least partly be present in deprotonated, anionic form. The phase transfer catalyst being present in both the organic and the aqueous phase, will then facilitate the reaction of the propargyl alcohol or propargyl alcoholate with the 4-chlorobenzyl chloride.

Preferred embodiments regarding the process of the invention are described hereinafter. The following general considerations apply to the process.

In general, the reaction steps are performed in reaction vessels customary for such reactions, e.g., conventional stirred tank reactors. The reactions may be carried out in a continuous or semi-batch-wise manner. Particularly preferably, the process of the invention is carried out in a semibatch-wise manner, wherein at least one reactant is provided in a reaction vessel and at least one further reactant is added over a certain dosing time.

In general, the process steps are preferably carried out under atmospheric pressure. Details regarding the reaction temperature are provided below. The end of the reaction can be monitored by methods known to a person skilled in the art, e.g., thin layer chromatography, GC, HPLC or NMR.

If not otherwise indicated, the reactants can in principle be contacted with one another in any desired sequence.

Furthermore, it is emphasized that the reaction steps may each be performed on a technical scale.

In the following preferred embodiments of the invention are provided. It is to be understood that the preferred embodiments of the invention are preferred alone or in combination with each other.

As indicated above, the present invention relates to a process for preparing a compound of formula I, as provided above, comprising a step (a) of reacting a compound of formula II, as provided above, with a compound of formula III, as provided above, in the presence of a base and a phase transfer catalyst, wherein the reaction mixture comprises at least two phases, wherein one phase is an organic phase and one phase is an aqueous phase.

In one embodiment of the invention, the process further comprises
  (b) optionally adding an organic solvent and/or water to the mixture obtained in the reaction step (a),
  (c) separating the at least two phases of the mixture obtained in step (a) or (b),
  (d) optionally washing the organic phase obtained in step (c) with an aqueous solution,
  (e) optionally extracting the aqueous phase obtained in step (c) with an organic solvent, and
  (f) isolating the compound of formula I from the organic phase obtained in step (c) or (d) and optionally in step (e).

As described above, in step (a) of the process of the invention, the reaction mixture initially comprises at least two phases, wherein one phase is an organic phase and one phase is an aqueous phase. The organic phase preferably comprises an organic solvent, the compound of formula II, and a proportion of the compound of formula III. The organic solvent is preferably selected from the group consisting of alkanes, aromatic solvents, ethers, and combinations thereof, and is more preferably an aromatic solvent, particularly preferably toluene. The aqueous phase preferably comprises water, a proportion of the compound of formula III and the base. The proportion of the compound of formula III in the aqueous phase may vary depending on the nature and concentration of the base in the aqueous phase. In particular, the solubility may be reduced at higher concentrations of an inorganic base in the aqueous phase. Further, it is to be understood that both the organic phase and the aqueous phase comprise a proportion of the phase transfer catalyst, as the phase transfer catalyst is soluble in both, the organic phase and the aqueous phase. The phase transfer catalyst facilitates the reaction of the compound of formula III or its deprotonated form, which is formed in the presence of the base in the aqueous phase, with the compound of formula II in the organic phase. Preferences regarding the base and the phase transfer catalyst as well as the amounts of the reactants, the base and the phase transfer catalyst in the reaction mixture have been provided above and will be provided in further detail below.

The mixture obtained in step (a) of the process of the invention, i.e. the mixture obtained after the reaction between the compound of formula II and the compound of formula III has been completed and the compound of formula I has been formed, may comprise at least one further phase, which is preferably a solid phase. In fact, this further phase is formed during the reaction of the compound of formula II and the compound of formula III as a byproduct of the formation of the compound of formula I. In particular, a chloride salt, preferably sodium chloride, is formed during the reaction step (a) of the process and preferably forms an additional solid phase to the extent that it is insoluble in the aqueous and organic phases.

Thus, in one embodiment of the process of the invention, the mixture obtained in the reaction step (a) comprises at least two phases, wherein one phase is an organic phase and one phase is an aqueous phase. In a preferred embodiment, the mixture obtained in step (a) of the process of the invention preferably comprises three phases, wherein one phase is an organic phase, one phase is an aqueous phase, and one phase is a solid phase, which is preferably a salt phase, particularly preferably a sodium chloride phase.

In connection with the mixture obtained in reaction step (a), it is preferred that the organic phase comprises an organic solvent as defined above, the compound of formula I, a proportion of the phase transfer catalyst, and optionally residual amounts of the compound of formula II and/or of the compound of formula III. It is to be understood that the residual amount of the compound of formula II is very low, preferably less than 1% by weight, preferably less than 0.5% by weight, more preferably less than 0.1% by weight, based on the total weight of the organic phase, as almost complete conversion of this reactant is achieved by the process according to the invention. The residual amount of the compound of formula III may be higher than the residual amount of the compound of formula II, as an excess of the compound of formula III is preferably used in reaction step (a). However, the residual amount of the compound of formula III may also partly be present in the aqueous phase.

Further, it is preferred in connection with the mixture obtained in reaction step (a) that the aqueous phase comprises water, residual amounts of the base, a proportion of the chloride salt, preferably the sodium chloride that is formed during step (a), a proportion of the phase transfer catalyst, optionally minor amounts of the compound of formula I, and optionally residual amounts of the compound of formula II and/or the compound of formula III. It is to be understood that the residual amount of the compound of formula II is very low, preferably less than 1% by weight, preferably less than 0.5% by weight, more preferably less than 0.1% by weight, based on the total weight of the aqueous phase, as almost complete conversion of this reactant is achieved by the process according to the invention. The residual amount of the compound of formula III may be higher than the residual amount of the compound of formula II, as an excess of the compound of formula III is preferably used in reaction step (a). However, the residual amount of the compound of formula III may also partly be present in the organic phase.

Further, it is preferred in connection with the mixture obtained in reaction step (a) that the solid phase comprises at least a proportion of the chloride salt, preferably the sodium chloride that is formed during step (a). It is to be understood that if no solid phase is present in the mixture obtained in reaction step (a), the chloride salt, preferably the sodium chloride that is formed during step (a), is present in the aqueous phase.

As described above, in optional step (b) of the process of the invention, an organic solvent and/or water is added to the mixture obtained in the reaction step (a). The organic solvent is preferably selected from the group consisting of alkanes, aromatic solvents, ethers, and combinations thereof, and is more preferably an aromatic solvent, particularly preferably toluene. Preferably, the organic solvent used in step (b) is identical to the organic solvent used in step (a).

Adding an additional amount of organic solvent and/or water, in particular water, can be advantageous, e.g., in order to dissolve a solid phase that is formed during the reaction as explained above. In particular, the addition of water is helpful to dissolve the salt, preferably the sodium chloride that is formed during the reaction process. Furthermore, adding an additional amount of organic solvent and/or water can also be advantageous in order to reduce phase separation times and/or obtain the phase transfer catalyst to a large extent in a separate phase. Preferably, water is added in suitably low amounts to avoid dissolution of the separate catalyst-containing phase. The formation of a separate catalyst-containing phase is advantageous for catalyst recycling, which is economically attractive in view of the high costs for the catalyst.

Thus, in one embodiment of the process of the invention, the mixture obtained in step (b) of the process of the invention comprises at least two phases, wherein one phase is an organic phase and one phase is an aqueous phase. In a preferred embodiment, the mixture obtained in step (b) of the process of the invention comprises three phases, wherein one phase is an organic phase, one phase is an aqueous phase and one phase is a catalyst-containing phase. Preferably, all three phases are liquid phases. Thus, while the mixture obtained in step (a) of the process of the invention preferably comprises two liquid and one solid phase as defined above, the mixture obtained in step (b) of the process of the invention preferably comprises three liquid phases.

In connection with the mixture obtained in step (b), it is preferred that the organic phase comprises an organic solvent as defined above, the compound of formula I, a proportion of the phase transfer catalyst, and optionally residual amounts of the compound of formula II and/or III. Preferably, the absolute amount of the phase transfer catalyst in the organic phase is small in comparison to the other phases present at that point in time. Particularly preferably, the organic phase comprises less than 30% by weight, preferably less than 20% by weight, more preferably less than 10% by weight of the total amount of the phase transfer catalyst that was added to the reaction mixture in step (a) of the process. A low amount of phase transfer catalyst in the organic phase is advantageous in terms of the isolation and purification of the compound of formula I.

Further, it is preferred in connection with the mixture obtained in step (b) that the aqueous phase comprises water, residual amounts of the base, the chloride salt, preferably the sodium chloride that is formed during step (a), a proportion of the phase transfer catalyst, optionally minor amounts of the compound of formula I, and optionally residual amounts of the compound of formula II and/or III. It is to be understood that the solid phase of the mixture obtained in step (a) of the process is preferably completely dissolved after step (b), so that the chloride salt, preferably the sodium chloride, is present in the aqueous phase in the mixture obtained in step (b). Further, it is to be understood that the proportion of the phase transfer catalyst in the aqueous phase depends on whether a separate catalyst-containing phase is formed in step (b). If a catalyst-containing phase is formed, the aqueous phase comprises less than 40% by weight, preferably less than 30% by weight, more preferably less than 20% by weight of the total amount of the phase transfer catalyst that was added to the reaction mixture in step (a) of the process. If no catalyst-containing phase is formed, the aqueous phase comprises up to 100% by weight of the phase transfer catalyst that was added to the reaction mixture in step (a) of the process. However, it is preferred according to the invention that a catalyst-containing phase is formed in order to allow catalyst recycling.

Thus, it is preferred in connection with the mixture obtained in step (b) of the process of the invention that a catalyst-containing phase is present. The catalyst-containing phase comprises the phase-transfer catalyst. Furthermore, the catalyst-containing phase preferably comprises water from the aqueous phase and organic solvent from the organic phase. In one preferred embodiment, the catalyst-containing phase comprises at least 60% by weight, preferably at least 70%, more preferably at least 80% by weight of the total amount of the phase transfer catalyst that was added to the reaction mixture in step (a) of the process. The amounts of water and organic solvent in the catalyst-containing phase may vary over a broad range. In one preferred embodiment, the catalyst-containing phase comprises from 35 to 55% by weight of the phase transfer catalyst, from 20 to 40% by weight of water, and from 5 to 15% by weight of organic solvent, in each case based on the total weight of the catalyst-containing phase.

In step (c) of the process of the invention, the at least two phases of the mixture obtained in step (a) or (b) are separated. In principal, step (c) may directly be performed with the mixture obtained in step (a), i.e. without performing step (b). However, if a solid phase is present in the mixture obtained in step (a), it is preferred that step (b) is performed before step (c) because the solid phase is disadvantageous for the phase separation step. Furthermore, it is preferred that step (b) is performed before step (c) because step (b) preferably results in a large proportion of the phase transfer catalyst being present in a separate catalyst-containing phase, which allows catalyst recycling.

Thus, in one embodiment of the process of the invention, step (c) comprises the separation of at least two phases of the mixture obtained in step (a). It is then preferred that only two phases are separated, namely the organic phase and the aqueous phase as defined above, but that no further solid phase is present. In another embodiment of the process of the invention, step (c) comprises the separation of three phases of the mixture obtained in step (b). It is then preferred that three phases are separated, namely the organic phase, the aqueous phase and the catalyst-containing phase as defined above.

It is to be understood in the context of the phase separation step (c) that the position of the layers of the phases will depend on the density. Thus, the phase with the lowest density will form the upper layer, and the phase with the highest density will form the lower layer. Preferably, the organic phase will form the upper layer and the aqueous phase will form the lower layer.

If a catalyst-containing phase is present, it will preferably form the intermediate layer. However, a different arrangement is also possible depending on the density of the two or three phases.

In optional step (d) of the process of the invention, the organic phase obtained in step (c) of the process is washed with an aqueous solution. It is to be understood that the term "washing" comprises washing one or more times, preferably one or two times with an aqueous solution. The term "aqueous solution" in the context of step (c) refers to water, preferably demineralized water, or an aqueous solution of an acid, preferably of a mineral acid such as hydrogen chloride or sulfuric acid. For example, an aqueous solution comprising from 0.02 to 0.2% by weight of sulfuric acid may be used.

The washing step is performed in order to remove residual amounts of the phase transfer catalyst and/or of the compound of formula III from the organic phase. The aqueous solution may change with regard to the pH value during the washing step to a more basic pH value as there is typically residual basic aqueous phase from the phase separation of step (c).

As a result of the washing step (d), the purity of the compound of formula I obtained by the process of the invention can be improved.

In optional step (e) of the process of the invention, the aqueous phase obtained in step (c) of the invention is extracted with an organic solvent. It is to be understood that the term "extracting" comprises extracting one or more times, preferably one or two times with an organic solvent. The organic solvent is preferably identical to the organic solvent that was used in the step (a) and optional step (b), and is preferably selected from the group consisting of alkanes, aromatic solvents, ethers, and combinations thereof, and wherein preferably the organic solvent is an aromatic solvent, particularly preferably toluene.

The extraction step (e) of the process of the invention has two advantages. First, residual amounts of the compound of formula I in the aqueous phase can be extracted and will be obtained in the organic phase. Isolation of the compound of formula I from this organic phase will increase the yield of the process. Second, the amount of total organic compounds (TOC) and even more the amount of adsorbable organic halides (AOX) in the aqueous phase can be reduced so that a cleaner wastewater is obtained. This leads to an improved process with regard to environmental aspects.

In step (f) of the process of the present invention, the compound of formula I is isolated from the organic phases obtained in step (c) or (d) and optionally in step (e). Thus, the compound of formula I may be isolated from organic phase obtained in step (c), or from the combined organic phases obtained in step (c) and in step (e), or from the combined organic phases obtained in steps (d) and (e).

In a preferred embodiment, the isolation of the compound of formula I in step (f) is performed by subjecting the organic phase(s) to a distillation process. The pressure for the distillation step is preferably from 500 mbar to 10 mbar, more preferably from 300 mbar to 20 mbar. The temperature of the distillation step is preferably from 20° C. to 130° C., more preferably form 50° C. to 120° C.

The compound of formula I can be isolated in high yields and in high purity, in particular if the compound of formula I is isolated from the combined organic phases obtained in steps (d) and (e).

In view of the above, optional steps (b), (d), and (e) of the process of the invention all provide certain advantages.

In one embodiment of the invention, the process therefore comprises step (b) of adding an organic solvent and/or water to the mixture obtained in the reaction step (a) as a mandatory step.

In another embodiment of the invention, the process comprises step (d) of washing the organic phase obtained in step (c) with an aqueous solution as a mandatory step.

In yet another embodiment of the invention, the process comprises step (e) of extracting the aqueous phase obtained in step (c) with an organic solvent as a mandatory step.

In one preferred embodiment of the invention, the process comprises steps (b) and (d) as mandatory steps.

In another preferred embodiment of the invention, the process comprises steps (b) and (e) as mandatory steps.

In yet another preferred embodiment of the invention, the process comprises steps (d) and (e) as mandatory steps.

In a particularly preferred embodiment of the invention, the process comprises steps (b), (d) and (e) as mandatory steps.

Accordingly, it is preferred according to the invention that the process, in addition to reaction step (a) further comprises
(b) adding an organic solvent and/or water to the mixture obtained in the reaction step (a),
(c) separating the at least two phases of the mixture obtained in step (b),
(d) washing the organic phase obtained in step (c) with an aqueous solution,
(e) extracting the aqueous phase obtained in step (c) with an organic solvent, and
(f) isolating the compound of formula I from the organic phase obtained in steps (d) and (e).

The above-described process provides the advantage that the reaction product is obtained in high yields and in high purity. Furthermore, the applied phase transfer catalyst can be recycled from the reaction mixture and used for further reactions according to the process of the invention, which provides an economical advantage. Moreover, the process is improved in terms of environmental aspects, as the amount of total organic compounds (TOC), and the amount of adsorbable organic halides (AOX) in the wastewater is low.

For catalyst recycling it is essential that a separate catalyst-containing phase is formed before step (c) is performed. As explained above, the catalyst-containing phase is preferably formed, if step (b) is carried out.

In a preferred embodiment of the invention, the phase separation step (c) therefore comprises the separation of three phases, wherein one phase is an organic phase, one phase is an aqueous phase and one phase is a catalyst-containing phase. Details regarding the three phases are provided above.

In another preferred embodiment of the invention, the process then further comprises isolating the catalyst-containing phase, and optionally recycling the catalyst-containing phase for repetition of the reaction.

The term "isolating" in connection with this embodiment means that, after separation in step (c), the catalyst-containing phase is, e.g., stored in a buffer tank, from where it may be charged again to the reaction vessel for another batch of the process of the invention. In any case, it is to be understood that the catalyst-containing phase itself may directly be used for performing step (a) of the process of the invention. In particular, it is not necessary to remove the organic solvent or water from the catalyst-containing phase. Preferably, no further work-up of the catalyst-containing phase is required for repetition of the process of the invention.

Further details regarding the nature of the phase transfer catalyst and the base as well as the amounts of the reactants, the base and the phase transfer catalyst in the reaction mixture and the reaction conditions for reaction step (a) of the process of the invention will be provided hereafter.

In one embodiment of the process of the invention, the phase transfer catalyst is a quaternary ammonium salt selected from the group consisting of benzyltrimethylammonium chloride, tetraethylammonium chloride, tetrapropylammonium bromide, tetrabutylammonium bromide, and tributylmethylammonium chloride. In a preferred embodiment, the phase transfer catalyst is a quaternary ammonium salt selected from the group consisting of tetrapropylammonium bromide, tetrabutylammonium bromide, and tributylmethylammonium chloride.

In one particularly preferred embodiment, the phase transfer catalyst is tetrapropylammonium bromide.

In another particularly preferred embodiment, the phase transfer catalyst is tetrabutylammonium bromide or tributylmethylammonium chloride, and especially preferably the phase transfer catalyst is tributylmethylammonium chloride.

Tributylmethylammonium chloride is particularly advantageous as phase transfer catalyst for the process of the invention, as this phase transfer catalyst allows the formation of a catalyst-containing phase, so that catalyst recycling is possible. Furthermore, tributylmethylammonium chloride has a good solubility in water, which makes the purification of the compound of formula I by performing a washing step according to step (d) of the process more effective. Moreover, tributylmethylammonium chloride is advantageous in terms of providing a high reaction speed, which is of particular relevance for large-scale application of the process.

In one embodiment of the process of the invention, the phase transfer catalyst is provided in a molar amount of from 0.5 to 20 mol-%, preferably 1 to 15 mol-%, more preferably 5 to 12 mol-% based on the molar amount of the compound of formula II.

In a preferred embodiment of the process of the invention, tributylmethylammonium chloride is provided in a molar amount of from 0.5 to 20 mol-%, preferably 1 to 15 mol-%, more preferably 5 to 12 mol-% based on the molar amount of the compound of formula II.

In one embodiment of the process of the invention, the base is selected from the group consisting of alkali carbonates, alkali hydroxides, and mixtures thereof.

In one preferred embodiment, the base is potassium carbonate, which is provided in the form of an aqueous solution in a concentration of from 40% to 50%.

In another preferred embodiment, the base is sodium hydroxide which is provided in the form of an aqueous solution in a concentration of from 10% to 50%, preferably from 25% to 50%, more preferably from 40% to 50%.

In one embodiment of the process of the invention, the base and the compound of formula II are provided in a molar ratio of from 3:1 to 1:1, preferably from 2.5:1 to 1.3:1, more preferably from 2.1:1 to 1.5:1.

Thus, it is advantageous, e.g., in terms of the reaction times, if an excess of the base is used as HCl scavenger in reaction step (a) of the process.

Furthermore, it has been found that higher concentrations of the base are advantageous in terms of the reaction times and the reduction of the formation of byproducts.

In one embodiment of the process of the present invention, the compound of formula III and the compound of formula II are provided in a molar ratio of from 2:1 to 1:1, preferably from 1.5:1 to 1:1.

It is advantageous to use a slight excess of the compound of formula III, i.e. the propargyl alcohol, in order to achieve complete conversion of the compound of formula II, as the unreacted compound of formula III remains in the aqueous phase and will therefore not contaminate the product, which is isolated from the organic phase.

In one embodiment of the process of the invention, the reaction step (a) is performed by providing a mixture comprising the compound of formula II and the phase transfer catalyst in an organic solvent, and adding the compound of formula III simultaneously with an aqueous solution of the base. It is to be understood that a proportion of the compound of formula III may also be present in the mixture comprising the compound of formula II and the phase transfer catalyst. Preferably, a proportion of from 1 to 25% by weight, preferably from 1 to 20% by weight, more preferably from 5 to 15% by weight of the compound of formula III, based on the total weight of the compound of formula III as used in reaction step (a), is present in the mixture comprising the compound of formula II and the phase transfer catalyst. On the other hand, a proportion of at least 75% by weight, preferably at least 80% by weight, more preferably at least 85% of the compound of formula III, based on the total weight of the compound of formula III as used in reaction step (a), is preferably added simultaneously with an aqueous solution of the base as indicated above.

Adding the compound of formula III and the base to a mixture comprising the compound of formula II and the phase transfer catalyst is advantageous in terms of the avoidance of byproducts as well as for safety reasons.

In principle, it is desired to add the compound of formula III and the aqueous solution of the base to the reaction mixture as fast as possible in order to reduce the overall reaction time needed for step (a) of the process of the invention and the level of byproduct formation. However, in view of the fact that the reaction is exothermic, a certain dosing time is needed especially in case of large-scale applications to limit the size and the cost of the cooling equipment. A skilled person will therefore adapt the dosing time depending on the batch size of the process, in order to achieve short reaction times, but limit size and cost of the cooling equipment.

In one embodiment of the process of the invention, the dosing time for adding the compound of formula III simultaneously with the aqueous solution of the base to the compound of formula II is from 0.5 to 3 hours, preferably from 1 to 2 hours.

The reaction between the compound of formula II and the compound of formula III is exothermic, so that the reaction mixture in step (a) of the process of the present invention is preferably cooled during the reaction step (a).

In one embodiment of the process of the present invention, the reaction step (a) is performed at a temperature within a range from 10° C. to 40° C., preferably from 15° C. to 35° C., more preferably from 20° C. to 30° C.

With regard to possible byproducts, it is a preferred embodiment to perform step (a) at lower temperatures. With regard to the reaction time, it is a preferred embodiment to perform step (a) at higher temperatures.

The present invention is further illustrated by the following examples.

EXAMPLES

The following abbreviations are used: CBC=4-chlorobenzyl chloride, POH=propargyl alcohol, PTC=phase transfer catalyst, BMC=tributylmethylammonium chloride.

Example 1: Catalyst Screening

A mixture of an aqueous sodium hydroxide solution (50%, 2 eq.), a PTC (0.1 eq.) according to Table 1 and toluene (200 g per mole CBC) was precharged in a reaction vessel. A mixture of CBC (16 g, 1 eq.) and POH (1.5 eq.) was added in 60 minutes at a temperature of 40° C. The results for the CBC turnover are provided in Table 1.

TABLE 1

| Entry | PTC | CBC turnover[a] |
|---|---|---|
| 1 | none | <1%[b] |
| 2 | BnMe₃NCl (solid) | 7% |
| 3 | Et₄NCl (solid) | 9%[c] |
| 4 | Pr₄NBr (solid) | 39%[d] |
| 5 | BMC (75% in water) | 94% |

[a]after dosing only 25% of CBC/POH (for safety reasons to prevent potentially dangerous accumulation) and 10-20 min post-stirring, turnover calculated from peak area (HPLC with UV detection at 205 nm) of CBC vs. 4-chlorobenzyl propargyl ether
[b]very pasty mixture, no improvement by doubling the amount of toluene
[c]PTC not completely dissolved; 38% CBC turnover when water is added (0.033 eq., 33% based on PTC)
[d]93% CBC turnover after 16 h

Example 2: Reaction with BMC as PTC and Formation and Isolation of the Catalyst-Containing Phase A mixture of toluene (100 g per mole of CBC), CBC (485 g, 1 eq.), BMC (0.1 eq.) and POH (0.11 eq.) was precharged in a reaction vessel at 30° C. NaOH (50% in H₂O, 2 eq.) and additional POH (0.99 eq.) were added simultaneously over 1 h at 30° C. Stirring was continued for another 3.5 h at 30° C. Toluene (150 g per mole of CBC) and water (200 g per mole of CBC) were added. After stirring for 2 min, a lower aqueous phase, an intermediate catalyst-containing phase (BMC content: 49% by weight by quantitative GC which is 84% by weight of the 0.1 eq. of BMC that was used for the reaction) and an upper organic phase were separated. This organic phase was washed twice with a solution of H₂SO₄ in water (first wash: 0.2% H₂SO₄ by weight, 204 g solution per mole of CBC, second wash: 0.05% H₂SO₄ by weight, 201 g solution per mole of CBC). Removal of low boilers by distillation under reduced pressure gave 4-chlorobenzyl propargyl ether in 92% yield (97% purity by quantitative GC).

The invention claimed is:

1. A process for preparing a compound of formula I

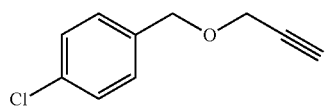
I comprising a step (a) of reacting a compound formula II

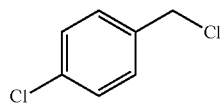
II with a compound of formula III

III in the presence of a base and a phase transfer catalyst in a reaction mixture,
wherein the reaction mixture comprises at least two phases, wherein one phase is an organic phase and one phase is an aqueous phase,
wherein the base is selected from the group consisting of alkali metal and alkaline earth metal hydroxides, alkali metal and alkaline earth metal oxides, alkali metal and alkaline earth metal carbonates, alkali metal and alkaline earth metal hydrogen carbonates, alkali metal and alkaline earth metal alcoholates, a tertiary amine, a pyridine, a bicyclic amine, and mixtures thereof, and
wherein the phase transfer catalyst is selected from the group consisting of benzyltrimethylammonioum chloride, tetraethylammonium chloride, tetrapropylammonium bromide, tetrabutylammonium bromide, and tributylmethylammonium chloride,
wherein the process further comprises
(b) adding an organic solvent and/or water to the mixture obtained in the reaction step (a),
(c) separating the at least two phases of the mixture obtained in step (b), and
(f) isolating the compound of formula I from the organic phase obtained in step (c),
wherein the phase separation step (c) comprises the separation of three phases,
wherein one phase is an organic phase, one phase is an aqueous phase, and one phase is a catalyst-containing phase,
wherein the process further comprises isolating the catalyst-containing phase.

2. The process according to claim 1, wherein the process further comprises
(d) washing the organic phase obtained in step (c) with an aqueous solution.

3. The process according to claim 1, wherein the process further comprises recycling the catalyst-containing phase for repetition of the process.

4. The process according to claim 1, wherein the isolation of the compound of formula I in step (f) is performed by subjecting an organic phases to a distillation process.

5. The process according to claim 1, wherein the phase transfer catalyst is provided in a molar amount of from 0.5 to 20 mol-% based on the molar amount of the compound of formula II.

6. The process according to claim 1, wherein the base and the compound of formula II are provided in a molar ratio of from 3:1 to 1:1.

7. The process according to claim 1, wherein the base is selected from the group consisting of alkali carbonates, alkali hydroxides, and mixtures thereof.

8. The process according to claim 7, wherein the base comprises sodium hydroxide.

9. The process according to claim 1, wherein the base is sodium hydroxide, which is provided in the form of an aqueous solution.

10. The process according to claim 1, wherein the organic phase comprises an organic solvent selected from the group consisting of alkanes, aromatic solvents, ethers, and mixtures thereof.

11. The process according to claim 1, wherein the compound of formula Ill and the compound of formula II are provided in a molar ratio of from 2:1 to 1:1.

12. The process according to claim 11, wherein the compound of formula Ill and the compound of formula II are provided in the molar ratio of 1.5:1 to 1:1.

13. The process according to claim 1, wherein the reaction step (a) is performed by providing a mixture comprising the compound of formula II and the phase transfer catalyst in an organic solvent, and adding the compound of formula III simultaneously with an aqueous solution of the base.

14. The process according to claim 13, wherein the dosing time for adding the compound of formula Ill simultaneously with the aqueous solution of the base is from 0.5 to 3 hours.

15. The process according to claim 1, wherein the reaction step (a) is performed at a temperature within a range from 10° C. to 40° C.

16. The process according to claim 1, wherein the phase transfer catalyst comprises tributylmethylammonium chloride.

* * * * *